United States Patent
Morton et al.

(10) Patent No.: US 10,653,632 B2
(45) Date of Patent: May 19, 2020

(54) BINDER POWDERS

(75) Inventors: David Morton, Victoria (AU);
Laurence Orlando, Victoria (AU);
Tony Qi Zhou, Victoria (AU); Louise Chia-Hua Ho, Victoria (AU)

(73) Assignee: Monash University (GB)

( * ) Notice: Subject to any disclaimer, the term of this patent is extended or adjusted under 35 U.S.C. 154(b) by 311 days.

(21) Appl. No.: 14/001,775

(22) PCT Filed: Feb. 28, 2012

(86) PCT No.: PCT/AU2012/000200
§ 371 (c)(1),
(2), (4) Date: Nov. 4, 2013

(87) PCT Pub. No.: WO2012/116402
PCT Pub. Date: Sep. 7, 2012

(65) Prior Publication Data
US 2014/0050795 A1  Feb. 20, 2014

Related U.S. Application Data

(60) Provisional application No. 61/447,349, filed on Feb. 28, 2011.

(51) Int. Cl.
*A61K 9/50* (2006.01)
*A61K 31/405* (2006.01)
*A61K 47/32* (2006.01)
*A61K 9/20* (2006.01)
*B27N 1/02* (2006.01)

(52) U.S. Cl.
CPC .......... *A61K 9/5015* (2013.01); *A61K 9/2013* (2013.01); *A61K 9/2027* (2013.01); *A61K 9/2095* (2013.01); *A61K 9/5089* (2013.01); *A61K 31/405* (2013.01); *A61K 47/32* (2013.01); *B27N 1/02* (2013.01)

(58) Field of Classification Search
CPC combination set(s) only.
See application file for complete search history.

(56) References Cited

U.S. PATENT DOCUMENTS

| | | | |
|---|---|---|---|
| 3,764,703 A | 10/1973 | Bergstrom et al. | |
| 5,994,324 A | 11/1999 | Ashida et al. | |
| 2003/0055075 A1* | 3/2003 | Rubsamen | 514/282 |
| 2003/0077297 A1* | 4/2003 | Chen et al. | 424/400 |
| 2005/0228075 A1* | 10/2005 | Gogos | C06B 21/0025 523/220 |
| 2010/0266703 A1* | 10/2010 | Morton | A61K 9/145 424/490 |

FOREIGN PATENT DOCUMENTS

| | | |
|---|---|---|
| GB | 2263910 A | 8/1993 |
| WO | WO-1999/059572 A1 | 11/1999 |
| WO | WO-2010/027404 A2 | 3/2010 |

OTHER PUBLICATIONS

Baklouti, S. et al.: "Compaction Behaviour of Alumina Powders Spray-Dried with Organic Binders", Journal de Physique III, Editions de Physique, Paris, France, vol. 6, No. 10, Oct. 1, 1996, pp. 1283-1291.
Search Report for EP Application No. 12752903.0, dated May 8, 2015, 2pp.
Kim, Ju-Young. et al.: "A Comparative Study Between Spray-Drying and Fluidized Bed Coating Processes for the Preparation of Pramipexole Controlled Release Microparticles for Orally Disintegrating Tablets", Drying Technology: An International Journal, vol. 32, No. Issue 8, 2014, Issued online, May 14, 2014, pp. 935-945.

* cited by examiner

Primary Examiner — Hasan S Ahmed
(74) Attorney, Agent, or Firm — Fishman Stewart PLLC

(57) ABSTRACT

The present disclosure relates generally to binder powders for use in powder material processing and processes for their preparation. The disclosure further relates to binder powders for use in making solid powder compact forms, solid powder compact forms containing said binder powders and methods for making solid powder compact forms.

20 Claims, 3 Drawing Sheets

BINDER POWDERS

CROSS-REFERENCES TO RELATED APPLICATIONS

This application is a U.S. National Phase Application of PCT/AU2012/000200, filed on Feb. 28, 2012, which claims the benefit of U.S. Provisional Application 61/447,349, filed on Feb. 28, 2011, the contents of which are both hereby incorporated by reference in their entirety.

TECHNICAL FIELD

The present disclosure relates generally to binder powders for use in powder material processing and processes for their preparation. The disclosure further relates to binder powders for use in making solid powder compact forms, solid powder compact forms containing said binder powders and methods for making solid powder compact forms.

BACKGROUND

The reference in this specification to any prior art publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

Controlled adhesion and cohesion of powders, including actions such as compression, compaction, densification, powder deposition, coating, adhesion or sintering are very common steps in the manufacture of solid powder forms of many functional or active agents such as pharmaceuticals, nutraceuticals, cosmetics, foods, detergents, inks, dyes, agricultural products and veterinary products. In each of the above, compatibility, compression, segregation, dispersion, adhesion, friction and flow are key factors, and depend on the surface properties, shape, deformation (including plasticity and elasticity), density, electrostatic (and other electronic) factors of the particles in the powder.

Compacts of solid dry powder forms are typically made by compressing a powder of particulate solid between two punches in a die of a compact press and subsequent ejection from the die. For the ingredients to be transformed into compacts of satisfactory quality, the formulation must have the key attributes of suitable flow, fluidity and compressibility. More specifically the powders to be compressed or compacted desirably have the following attributes:

Flow: the powder particles must flow into the die space of the press sufficiently rapidly and in a reproducible manner. The weight of the compact, and hence the dosage of active or functional agent, is dependent upon the volume of material which fills the die and unless the material flows freely into the die, unacceptable variation in compact weight, homogeneity in structure and content may ensue;

Cohesion: the particles must cohere when subjected to a compressing force, and that coherence should remain after the compressive force has been removed, otherwise after compression the compact will crumble and fall apart on handling; and Lubrication: after the compression event is complete, it must be possible for the compact to be removed freely from the press without damage to either the compact or the press.

Very few powdered functional or active ingredients possess all of these attributes in their original state, and indeed many possess none. Thus these materials generally require significant processing and subjection to treatments with other additive materials, such as diluents or fillers; binders (which are used to bind the powders together); disintegrants (which help the compacts to break up and dissolve); glidants (which are used to improve granule flow); anti-adherents or lubricants (which help the release of the compressed compact from the die); and anti-adhesives (which are sometimes used to prevent film residue being left on the die/punch) in order to achieve powders with the desired characteristics for solid form manufacture.

One method of addressing this is the process of granulation, or size enlargement, which is often required in order to achieve the necessary characteristics of flow and subsequent compression into tablet forms that adhere together in a structure that is strong enough to undergo subsequent processing, storage and ultimate handling and delivery.

In wet granulation, the process generally involves addition of several excipients in substantial quantities, and the use of a liquid (typically water) to aid the formation of a granule, often including a binder in solution. Not only does the complexity of this process make it costly (in terms of the number of steps, time, of equipment, of energy consumption, of materials), the addition of water to an active or functional agent which is moisture-sensitive increases the risk of decomposition. Furthermore, heat is then required to dry the granules, again with risk of decomposition of the active or functional agent.

In dry granulation, although water is avoided, the process also generally involves addition of several excipients in substantial quantities. The mixture is blended and then passed through a partial compaction process to form a ribbon, which is then milled into suitable granules. Again, the complexity of this process makes it costly, in terms of the number of steps, time, equipment, energy, and materials.

In these processes, the excipients often need to be added in significant quantities to allow the tablet ingredients to compact and bind together effectively on compression. The resulting tablets are often notably large, especially where high doses of the active or functional agent are required to be delivered, and for pharmaceutical dosage forms intended for oral administration, such large tablets may present patients with swallowing difficulties.

Tablet-like forms may also be made by a hot-melt extrusion, whereby the active agent is contained within a deformable polymer which can be extruded, such as polyvinylpyrrolidone (PVP). However, again this requires a significant mass of polymer, and the process requires the use of heat which may be disadvantageous.

Direct compression of the component powders can potentially overcome some of the disadvantages associated with granulation processes, as only prior blending of powders is required. However, in practice, the component powders (e.g. active agent, filler or carrier, binders, lubricants etc) often vary in size, shape, density and degree of cohesiveness, and typically an interactive mixture is obtained, wherein the cohesive particles adhere to free-flowing particles. Again, often only a very low level of active agent can be incorporated. Further, using known binder powders, the flow of such small sized powders is usually very poor, as these are too cohesive to blend efficiently to the other powders of the formulation in order to fill the compact dye with sufficient consistency.

In each of these cases, the powder composition and structure needs to be such that during compression, significantly strong bonding is formed between the particles. The formation of such bonds under compression follows a process of plastic and elastic deformation and/or fracture, which must then form these strong bonds between the particles to ensure that the tablets are sufficiently strong to avoid breakage or other faults during production, handling, transport and storage.

There are few real alternatives to these approaches currently used, despite the fact that substantial limitations exist in all cases, and that solid pharmaceutical oral dosage forms are by far the most common form of medication. Additives and/or processes which allow for improvements in both the product form as well as simplification of the manufacturing process, are therefore highly desirable.

SUMMARY

Throughout this specification and the claims which follow, unless the context requires otherwise, the word "comprise" and variations such as "comprises" and "comprising", will be understood to imply the inclusion of a stated integer or step or group or integers or steps but not the exclusion of any other integer or step or group or integers or steps.

The singular forms "a", "an" and "the" include plural aspects unless the context clearly dictates otherwise.

All aspects, embodiments and examples described herein are encompassed by the term "invention".

It has now surprisingly been found that binder particles that are at least partially coated with, or comprise at their surface, a non-cohesive surface coating material may afford one or more advantages over non-coated binder particles, particularly when used in making solid powder compressed, or compacted dosage forms. In certain embodiments these may include one or more of: improved powder flow through reduced cohesiveness; reduced requirements for binders and/or other excipients, such as carriers; improved strength or hardness of the solid powder compacts formed from such powders; circumvent the need for complex granulation steps; and reduced adhesion of such compacts when removed from the die.

The coated binder particles described herein possess relatively low adhesion and cohesion when in contact with other powders and thus advantageously can be easily mixed into a dry powder blend and form a coating or partial coating on the surface of other powders, such as carriers and active or functional ingredients, to be compacted.

Accordingly, there is provided a binder powder comprising binder particles wherein at least a portion of the surface thereof is coated with a non-cohesive surface coating agent.

In further embodiments thereof, at least 80% of the coated binder particles have a size of about 50 µm or less.

In some embodiments, the binder is polyvinylpyrrolidone (PVP).

In some embodiments, the non-cohesive surface coating agent is L-leucine.

In further embodiments, the binder is PVP and the non-cohesive surface coating agent is leucine.

The coated binder powders may be used in the formulation of solid powder compacts of an active or functional ingredient. Thus, in a further aspect the disclosure also provides a solid powder compact form of an active or functional ingredient, comprising a binder powder as disclosed herein.

In some embodiments, the binder powder is mixed or blended with an active or functional ingredient, and optionally, one or more further additives, prior to compaction or compression. In further or other embodiments, the binder particles disclosed herein may advantageously circumvent the requirement for blending a binder powder with an active or functional ingredient prior to compaction or compression by the incorporation the active or functional ingredient into the binder particles.

In another embodiment, there is provided a binder powder which comprises binder particles wherein at least a portion of the surface thereof is coated with a non-cohesive surface coating agent and which particles further comprise a functional or active ingredient.

In another aspect, there is provided a process for manufacturing a solid powder compact form of an active or functional ingredient comprising the step of compacting a dry powder formulation which comprises a binder powder as disclosed herein.

In another aspect there is provided the use of a binder powder as disclosed herein in the manufacture of a solid powder compact form of an active or functional ingredient.

In one embodiment, there is provided a process for manufacturing a solid powder compact form of an active or functional ingredient comprising:
(i) blending a powdered active or functional ingredient, and optionally one, or more further powdered additives, with a binder powder comprising binder particles wherein at least a portion of the surface thereof is coated with a non-cohesive surface coating agent; and
(ii) compacting said blended powders to form a solid powder compact form of the active or functional ingredient.

In some other embodiments, the disclosure relates to a process for manufacturing a solid powder compact form comprising the step:
(i) compacting a binder powder, comprising binder particles wherein at least a portion of the surface thereof is coated with a non-cohesive surface coating agent and which particles further comprise a functional or active ingredient and optionally one or more further additives, to form a solid compact form of the active or functional ingredient.

Further aspects provide solid powder compact forms prepared by the processes of the disclosure.

Further embodiments relate to a method of preparing coated binder particles comprising spray-drying a mixture of binder and a non-cohesive surface coating agent. The mixture may optionally contain one or more functional or active ingredients and/or one or more further additives.

DETAILED DESCRIPTION OF SOME EMBODIMENTS

Figure 1A:
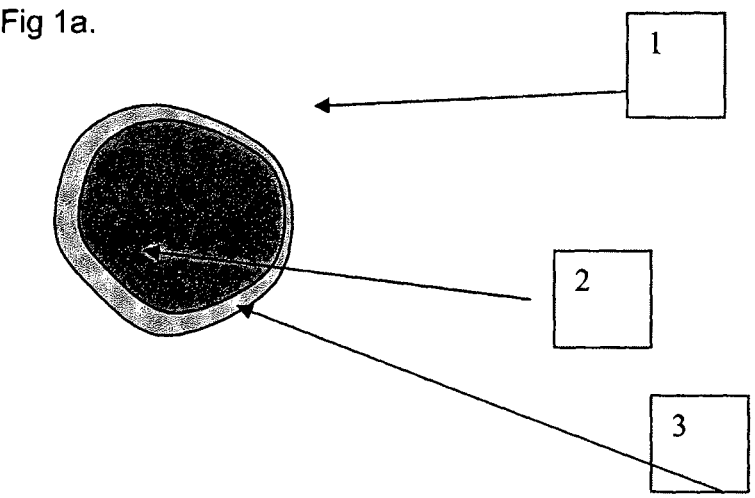
FIG. 1a graphically illustrates an exemplary binder powder (1) having a binder particle core (2) and a surface coating (3).
Figure 1B:
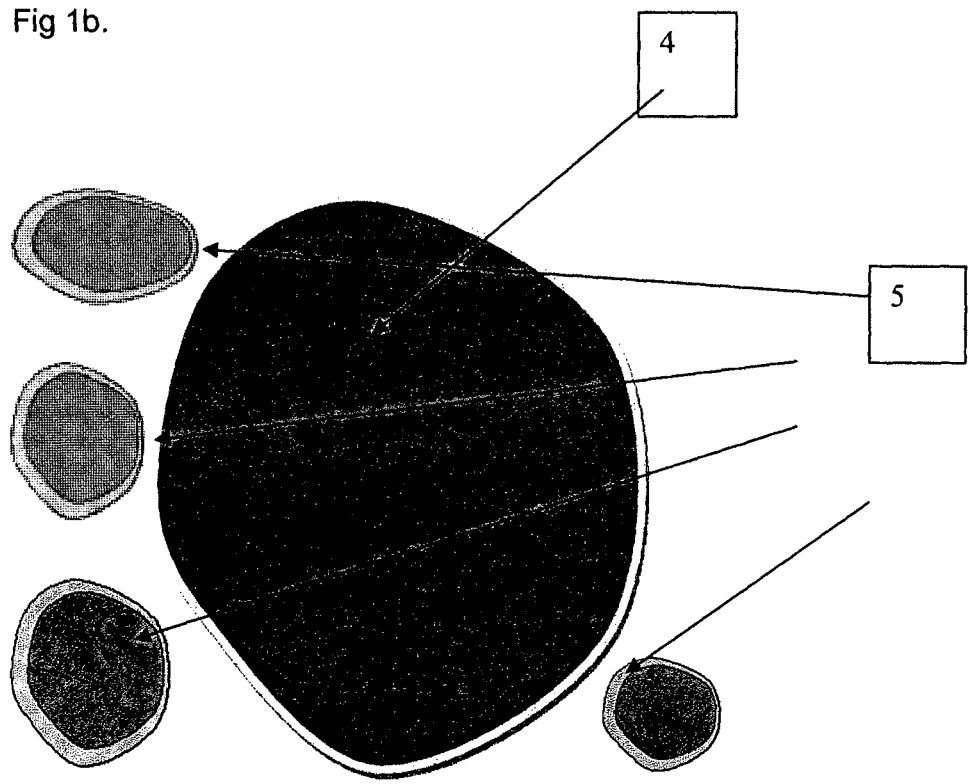
FIG. 1b graphically illustrates the coated particles (5) adhering to the surface of the drug particle (4) after blending.
Figure 2:
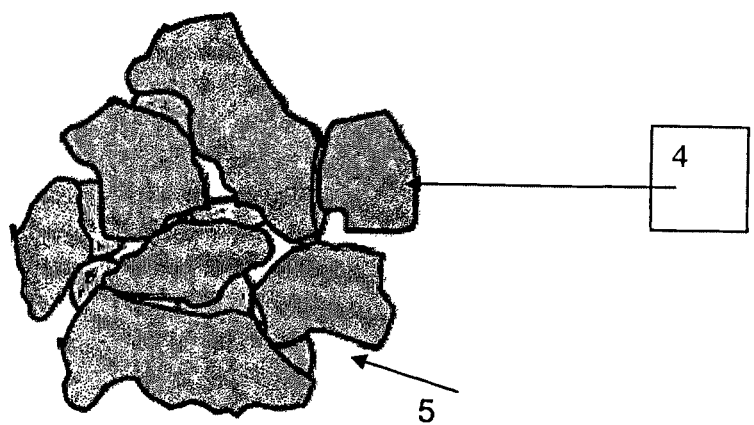
FIG. 2 graphically illustrates a cross-section of a compacted binder powder and drug particles, whereby the binder particles form adhesive links between the drug particles.

The disclosure herein relates to coated binder powders for use in the manufacture of solid powder compact forms (also referred to herein as "compacts") containing an active or functional ingredient, and optionally other additives.

As used herein, the term "powder" and variants such as "powdered" refers generally to a solid in a finely dispersed particulate form. The powder may be any suitable form, such as amorphous, crystalline or granular, and prepared by any suitable method such as precipitation; crystallization; spray-drying; grinding, milling or other size reduction means; and granulation. The binder powders of the disclosure are discussed in further detail hereinafter.

As used herein, the term "binder" includes any additive which imparts cohesive qualities and is used for the purpose of binding or holding together the powdered components in a solid compacted form. Suitable binders depend on the individual application and active or functional ingredients and are known to, and can be determined by, the person skilled in the art.

In some embodiments, the binders contemplated are those suitable for the manufacture of solid pharmaceutical dosage forms. Any binder which is known to be suitable for use in dry powder tabletting, granulation or hot melt extrusion is contemplated by the disclosure. Some non-limiting examples of suitable binders may include: sugars (e.g. lactose, sucrose, glucose and dextrose); gelatine; dibasic calcium phosphate; corn (maize); starch; pre-gelatinized starch; acacia; xanthan gum; tragacanth; gelatine; alginic acid; cellulose, microcrystalline cellulose, polymers, co-polymers or mixed polymers of any range of molecular weight, including: polyethylene glycol, polyvinyl alcohols, polyvinylcaprolactam, polymethacrylates, polyvinylpyrrolidone (PVP) and copolymers such as polyvinylpyrrolidone-vinyl acetate (PVP-VA), for example Kollidon VA64 as manufactured by BASF, or polyvinylcaprolactam-polyvinyl acetate-polyethylene glycol, for example Soluplus™ as manufactured by BASF, and mixtures of polymers, such as mixed polyvinylpyrrolidone and polyvinyl acetate, for example Kollidon SR as manufactured by BASF, and modified celluloses such as hydroxypropyl methylcellulose (HPMC), methyl cellulose, ethyl cellulose, hydroxylpropyl cellulose (HPC), such as Klucel as manufactured by Aqualon, hydroxyethylcellulose (HEC), ethyl cellulose and sodium carboxy methyl cellulose. Examples also include Carbopol polymers which are polymers of acrylic acid cross-linked with polyalkenyl ethers or divinyl glycol and other Carbomers. In certain embodiments, the binder contemplated herein is polyvinylpyrrolidone (PVP, or povidone). The polymer is not limited to any particular weight range, but exemplary polymers, for example polyvinylpyrrolidone, may have molecular weights of about 2000, 10,000, 50,000, and 1,000,000. Other binders are known in the art; for example as described in *Handbook of Pharmaceutical Excipients*, Eds, Raymond C. Rowe, et al 5$^{th}$ Edition. It will be appreciated that although an additive may primarily be selected for use as a binder, this does not prevent it from performing one or more additional functions within the formulation, e.g. disintegrant, lubricant, glidant, delayed release agent etc.

In some embodiments it may be advantageous for the binder to be water soluble or wettable, such that it can be spray dried from an aqueous system and also dissolution of the resulting material is not retarded.

The term "non-cohesive surface coating agent" refers to an agent capable of at least partially coating, or forming the surface of, binder particles such that the particles do not substantially aggregate or stick together. Thus, the surface of the coated binder particles have a substantially reduced cohesion compared to non-coated particles. In certain embodiments, the reduction in cohesion may be at least about 20%, 30%, 40%, 50%, 60%, 70%, 80% or 90%.

Cohesion may be measured by powder shear testing (see for example Schwedes J. et al., *Granular Matter*, 2001, 5:1-43).

Some exemplary, but not limiting, non-cohesive surface coating agents contemplated include film-formers, surfactants and lubricants, such as used in the art of solid pharmaceutical dosage manufacture. Some non-cohesive surface agents contemplated herein include $C_6$-$C_{35}$ fatty acids, their salts, esters and other derivatives, including saturated and unsaturated (cis and trans) forms. Some examples thereof include stearic acid, magnesium stearate, calcium stearate, zinc stearate, sodium stearate, sodium stearyl fumarate (PRUV), sodium stearyl lactylate, sodium lauryl sulphate, palmitates and behenates, (e.g. glyceryl behenate, also known as Compritrol). Other non-cohesive surface agents include amino acids (such as L-leucine and isoleucine), derivatives of amino acids, including their salts or esters or perptides (including trileucine), lipids and phospholipids (such as lecithin, DPPC: di-palmityl phosphatidylcholine, DPPI: di-palmityl phosphatidylinositol and DPPE: di-palmityl phosphatidylethanolamine, hydrogenated vegetable oil and polyethylene glycol.

Film forming materials include gum Arabic, hydroxypropyl methyl cellulose and other cellulose derivatives.

Alternatively, inorganic lubricants may be added to the binder surface as the non-cohesive surface coating agent, in a separate step which may be a blending step. Examples include inorganic lubricants such as colloidal silica (such as a Carbosil grade or an Aerosil grade), colloidal alumina, colloidal titania and talc as well as inorganic particles in the sub-micron size range from 1 nm to 1 μm such as titania, alumina, iron oxide, zinc oxide, including any fumed metal oxide nanoparticles. In such nanoparticles it is proposed that the nanoparticles can lubricate constituent fine powders to provide flow, yet, when under compression, may be pressed below the surface of the coated particles, removing them from the surface contact barrier role, again yielding sufficient particle-particle contacts to form strong tablets. In addition, these inorganic nanoparticles may be surface treated to be made hydrophobic or hydrophilic, or surface modified with polymeric additives.

For the avoidance of doubt, reference to the abovementioned materials includes any polymorph, and hydrate of these materials, from any source of such material, including synthetic, vegetable, mineral or animal.

Other film-formers, surfactants and lubricants are known in the art; for example as described in *Handbook of Pharmaceutical Excipients*, supra.

In certain embodiments the non-cohesive surface agent contemplated herein is L-leucine (leucine), trileucine or isoleucine. One example is L-leucine.

As used herein, the term "size" when used in reference to particles, such as the coated binder particles, refers to that measured in terms of a volume equivalent spherical diameter (VESD). For example, where a particle is described as having a "size" of 50 μm, it refers to a volume equivalent spherical diameter of 50 μm. The equivalent spherical diameter of an irregularly-shaped object is the diameter of a sphere of equivalent volume. VSED may be measured by any suitable measuring means commonly used in particle sizing. The equivalent diameter of a non-spherical particle is equal to the diameter of a spherical particle that exhibits an identical property, e.g. aerodynamic, light scattering or optical. In the case of particles being measured by laser diffraction, the diameter of the sphere that yields an equivalent light scattering pattern to the particle being measured is reported, which to a reasonable approximation corresponds to a sphere of equivalent average cross-sectional area. Particle sizing measurements may be made by a laser diffraction method, in either a dry or liquid suspension. Such measurements are well known as made by instruments such as the Malvern Mastersizer 2000 (Malvern instruments UK), or the Sympatec Helos (Sympatec GmbH, Germany). These instruments measure the volume equivalent spherical diameter, as outlined above, and then the measurements of multiple particles are combined by the instrument software to provide volume based cumulative particle size distributions. Such distributions can be used to identify the volume equivalent spherical diameter for which a percentage by mass or volume is less than.

It will be appreciated that binder powder particles for use in blending with another component before compaction or compression are advantageously smaller than the particle size of the other component such that it allows the coated binder particles to spread over or coat the surface of the other components such as the active or functional ingredient or other additives, such as carriers and diluents, for example, as an interactive mixture.

Advantageously, in some embodiments, at least 80% by mass of the coated binder particles contemplated herein have a volume equivalent spherical diameter of about 50 µm or less. In further embodiments, at least 80% or 85% by mass have a volume equivalent spherical diameter of about 30 µm or less, or even about 20 µm or less, about 15 µm or less, about 10 µm or less or about 5 µm or less. In some embodiments, at least 90% or 95% by mass of the coated binder particles have a volume equivalent spherical diameter of about 30 µm or less. In still some further embodiments, at least 90% or 95% or 99% by mass of the coated binder particles have a volume equivalent spherical diameter of about 20 µm or less, about 15 µm or less, about 10 µm or less or about 5 µm or less.

The non-cohesive surface coating agent forms a coating on (or coats) the binder core particle, which coating may be substantially continuous or discontinuous. It will be appreciated that it is not necessary for the entire surface of the binder particle to be coated provided that the particles exhibit the desired non-cohesiveness. In certain embodiments the coating covers, on average, at least 40% or 50% of the binder core (that is, at least 40% or 50% of the total surface area of the binder core will comprise or be covered by the non-cohesive surface coating agent). In further embodiments, at least 70% or at least 80% of the surface of the binder core is coated. In still further embodiments at least about 90%, about 95% or about 100% of the surface of the binder core particles coated.

In some embodiments the coating is advantageously on average less than about 5 µm thick, for example less than about 1 µm, less than about 0.5 µm, less than about 0.2 µm, less than about 0.1 µm, less than about 50 nm, less than about 20 nm or less than about 10 nm thick. Thickness may be determined by any suitable means in the art. It is possible to obtain approximate semi-quantitative extent of thickness (such as those values above) of the coatings on particles using state of the art time-of-flight secondary ion mass spectrometry (TOF SIMS), or x-ray photoelectron spectroscopy, or transmission electron microscopy (TEM).

The binder particles of the disclosure may advantageously be used to prepare solid powder compacts of an active or functional agent. One or more active or functional agents may be present in the solid powder form. In some embodiments, an active or functional agent (and optionally any further additives) is intimately and uniformly blended with the binder powder, prior to formation of the solid powder compact. In some embodiments, the active or functional agent is incorporated into the binder particles. One or more active or functional ingredients may be present and the binder particles and/or solid powder forms may also further comprise additives such as disintegrants, controlled release agents, lubricants, glidants, fillers, carriers or diluents, stabilizers, preservatives, surfactants, buffers, flavours, and colours.

Thus, the disclosure further provides a process for the manufacture of a solid powder compact form comprising the step of compacting a binder powder comprising binder particles wherein at least a portion of the surface thereof is coated with a non-cohesive surface coating agent and wherein said binder particles optionally further comprise one or more functional or active ingredients. In further embodiments, the binder powder is first blended with one or more functional or active ingredients and/or additives prior to compaction.

The active or functional agent can be any agent intended for effecting a desired result or function upon administration, application or delivery. Examples include, but are not limited to, dyes, detergents; agrochemicals (e.g fertilizers, nutrients, pesticides, fungicides, insecticides); foodstuffs, including sweeteners; as well as pharmacologically active agents, for veterinary or human use, including drugs, nutraceuticals, and other nutrients, such as amino acids, vitamins and minerals.

In some embodiments, the active or functional agent is a pharmacologically active agent. Pharmacologically active agents contemplated herein include any drug or agent which exerts a pharmacological or physiological effect when administered to a human or animal subject, such as when used in the treatment, management or prophylaxis of a disease of condition, and which are suitable for delivery in a solid powder compact form. Non-limiting examples of such agents include: antimicrobials (e.g. anti-bacterial, anti-viral, anti-fungal), analgesics, anti-depressants, anti-psychotics, anti-inflammatories, anti-arrhythmics, anti-coagulants, anti-cholesterols, anticonvulsants, anti-spasmodics, anti-arthritics, anti-ulcer agents, anti-hypertensives, anti-diabetics, diuretics, sedatives and tranquilizers, amino acids, minerals, and vitamins.

Thus, in some embodiments the disclosure relates to pharmaceutical (human or veterinary) dosage forms for administration to human or animal subjects. The dosage form may be in any form suitable for administration to the subject (e.g. orally, lingually, buccally, by bolus injection or surgical implantation/insertion, vaginally, or rectally). The solid powder compact forms contemplated herein include, but are not limited to: tablets, caplets, minitabs, troches, inserts, implants, boluses and any other solid powder delivery forms known in the art. Still further embodiments relate to solid pharmaceutical dosage forms for oral administration. In yet other embodiments, transdermal dosage forms are contemplated. These may comprise compacts which can be applied to the skin and held in place by a suitable device, such as a patch, for example, microneedles, built into a patch or similar device which can be applied to the skin.

It will be appreciated that where the solid powder compact form is intended for animal or human use, any further additive will be pharmaceutically acceptable in the sense that it is compatible with the other components of the formulation and not injurious to the subject. Some non-limiting examples thereof include pharmaceutically acceptable disintegrants, controlled release agents, lubricants, glidants, fillers, carriers or diluents, stabilizers, preservatives, surfactants, buffers, flavours, sweeteners and colours. Further examples are known in the art (see for example *Hand-* book of *Pharmaceutical Excipients*, supra and *Remington: The Science and Practice of Pharmacy*, 21$^{st}$ Edition,).

In still further embodiments one or more functional or active ingredients may be incorporated into the binder particles, optionally with one or more additives. The binder powder may then be blended with a further, same or different, functional or active ingredient, and/or with one or more additives. Alternatively, the resulting powder may be directly compressed or compacted i.e., alone, in the absence of further functional or active ingredients or additives being blended with the binder powder. Such a process may advantageously avoid or reduce the need for large quantities of excipients, diluents or carriers.

The process of compacting dry powder ingredients, such as in the manufacture of human or veterinary pharmaceutical dosage forms, is well known, for example, as described in *Remington, "The Science and Practice of Pharmacy"*, supra. Briefly, the process involves a number of steps: filling of the die in which the powder is accurately measured out to ensure accurate weight and dosage; compression, where pressure is applied to form the powder into a solid; and ejection, where the tablet is ejected from the die.

In some embodiments the coated binder particles may advantageously be added to other components of a powder composition for compaction in an amount of about 50 wt %, or less of the entire composition. In further embodiments, the coated binder particles are advantageously added to the other components of the powder composition in an amount of about 30 wt %, 20 wt %, 15 wt %, 10 wt % or 5 wt % or less. In other embodiments the binder particles are added in an amount of about 90 wt %, 80 wt %, 75 wt %, 70 wt %, or 60 wt %. In further embodiments the binder particles make up 100 wt % of the powder formulation for compaction.

In some embodiments, the coated binder particles may be prepared by spray-drying a liquid mixture of the binder and the non-cohesive surface coating agent, optionally together with one or more active or functional ingredients, such as pharmacologically active agents and or pharmaceutically acceptable additives, such that on spray-drying, fine particles are formed with a binder core and a coating of the non-cohesive surface coating agent. These other components may be in the form of solid solutions, or solid suspensions within the dried binder particles.

Thus, in a further aspect, there is provided a method of preparing coated binder particles comprising spray-drying a mixture of binder and a non-cohesive surface coating agent. The spray-dried coated particles may further comprise an active or functional ingredient.

Methods for spray-drying are well known in the art. The term "spray-drying", or variants such as "spray-dried" is intended to encompass any process in which a solution or suspension is formed in a liquid, whereby the liquid is physically atomised into individual droplets which are then dried to form a dry particulate powder. It may encompass any form of a droplet to particle formation process, and may encompass related processes such as spray-freeze drying, spray chilling and spray flash drying. The droplets may be formed by any known atomisation process, including but not limited to pressure atomisation, pneumatic atomisation, two or multiple fluid atomisation, rotary disc atomisation, electrohydrodynamic atomisation, ultrasonic atomisation, and any variant of such atomisation processes. The atomisation may occur from one spray source or multiple sources. The liquid mixture may be aqueous, that is the liquid phase contains from about 10 v/v % up to 100 v/v % water (e.g. 30, 50 or 80 v/v %), or may be substantially non-aqueous, that is where the liquid phase contains less than 10 v/v % of water and may optionally comprise co-solvents, which may be water-miscible, such as ethanol, plus additional components dissolved or suspended therein. The liquid may include a material that is a vapour or solid at ambient conditions but exists as a liquid under the selected process conditions. The spray-dried particles may be further dried before use. The droplets formed may be dried by applying heat in the form of a heated drying gas, or heat may be applied in other ways, for example radiating from walls or as microwaves. Alternatively drying may be achieved by freezing followed by drying or by application of vacuum.

In further embodiments, the process comprises spray-drying an aqueous suspension or solution of binder and non-cohesive surface coating agent, optionally together with one or more pharmacologically active agents and or pharmaceutically acceptable additives.

The coated binder particles may also be formed by other techniques well known in the art for particle engineering, such as precipitation, condensation or milling. Alternatively, the binder particles may be coated with the surface coating agent by a separate subsequent process, such as blending, vapour phase condensation, liquid phase precipitation or co-milling.

In some embodiments, the weight ratio of binder to non-cohesive surface coating agent is about 60:40, 65:35, 70:30, 75:25 or 80:20. In still further embodiments, the ratio is 90:10, 95:5, 98:2 to 99:1 or even 99.9 to 0.1. Alternatively, the amount of non-cohesive surface coating agent may be expressed as wt/wt %, of binder, for example, 1%, 2.5%, 5%, 7.5%, 10%, 12.5%, 15%, or 20%.

In certain embodiments, the powders comprising the coated particles of the invention may have improved flow characteristics when compared to uncoated binder particles. This is advantageous at the filling stage of the manufacture of the solid powder compact as it allows for improved accuracy and consistency in measurement of the powder into the die, and consequently, exact and accurate dosing of the active or functional ingredient.

Generally in any powder manufacturing process, powder must flow, from a hopper into the feed frame of a compact machine. The powder may flow under gravity, optionally with some agitation, but resisting segregation. The powders should resist faults such as "bridging", "badger splitting" or "rat-holing". In some embodiments, the coated binder powders described herein overcome or at least partially ameliorate these problems as the coating provides for improved fluidity.

Additionally, the flow must ensure that the die cavity is filled consistently, completely and uniformly. In certain advantageous embodiments, the coated binder particles described herein allow small near spherical particles to be used, although other shapes may also be used in the invention, such as plates, needles, and angular or other irregular forms. Advantageously, spheres offer minimum interaction with walls of the compact machine and provide flow uniformly.

In some embodiments the binder particles described herein may reduce the tribo-electric charging of the powder such that the materials have a reduced or minimum electrostatic charge.

Some spread in particle size may be advantageous to provide a size distribution with good packing efficiency. Bi- or multi-modal size distributions may be advantageously used, which are known to provide more efficient packing.

In some further embodiments, the powder density of the coated binder particles is higher than uncoated particles of comparable materials with the same size distribution. This may be bulk aerated density or tapped density, as measured according to the United States Pharmacopeia. Preferably the measurement is bulk aerated density. For example, the coated binder particles may be at least 25% denser, 40% denser, 70% denser, and 100% denser, and 125% denser to as much as 150% denser or more compared to uncoated materials.

In some embodiments, the powder Hausner ratio of the coated binder particles is lower than uncoated particles of comparable materials with the same size distribution. This may be determined from the bulk aerated density and bulk tapped density, as measured according to methods outlined by the United States Pharmacopeia. For example, coated materials disclosed herein may have Hausner ratios reduced by about 5%, through to about 10%, or 20%, to as much as about 50% reduced or more compared to uncoated materials. The absolute values of the Hausner ratios of the treated powders may be less than about 1.5, 1.4, 1.35, 1.3 or even 1.25.

Hausner ratio is a well established measure of powder flow. In some embodiments, the coated binder particles described herein may advantageously demonstrate an improvement in powder flow properties. This improvement may be measured in a number of ways, known to those skilled in the art. These include, but not limited to, the Carrs index (for example, the absolute values of the Carrs Index of the treated powders may be less than 0.40, 0.35, 0.30, 0.28, or even 0.25), Angle of repose (for example, the absolute values of the angle of repose of the treated powders may be less than 50, 40, 35, 30 or even 27 degrees), FlowRatex, ring shear testing, and Freeman FT4 powder rheometer. In certain embodiments the improvement may result in reduced cohesion measurements such as determined by shear testing. Thus, a quantitative level of improvement may be determined by quantitative measurement and comparison to uncoated particles. In some embodiments, the coated binder particles may demonstrate an improvement in a property by at least 10% or at least 20% or at least 50% or at least 70% or at lest 90% or 100% or at least 150% or 200%.

In some embodiments the coated binder particles described herein may advantageously allow for the use of small size particles of multi-component compositions that resist segregation. Segregation is reduced because either a stable structured or ordered mix results or because all particles are approximately in the same or sufficiently similar or overlapping particle size distributions.

In some embodiments, the binder particles described herein additionally may allow particles to be coated to provide specific properties, including rapid dissolution, rapid wetting, rapid disintegration, delayed dissolution, and timed release by selection of the coating material.

The coating process may allows for reduction in the influence of plastic/elastic deformation properties of the host materials, and consequently may allow for the facile compaction of otherwise difficult to compact materials.

In some embodiments, the solid powder compact or powder may be subsequently heated to remove any surface additive, or any other volatile or decomposable constituent. This may or may not leave voids in the structure which may have some functional benefit, such as controlled porosity.

In some embodiments, the coating process also increases the stability of composite components by reducing any interactions or unwanted chemical or physical reaction with other components at any stage of manufacture or storage. The powders of the invention may also be used to form composite compacts such as multilayered compacts.

In still other embodiments, the compacts may be further coated such as film-coated or enteric-coated, using suitable coatings known in the art.

The disclosure also contemplates multiple compressed solid powder dosage forms which have undergone more than one compression cycle to produce multi-layered or multi-coated coated forms. The various layers may contain the same or different functional or active agents and/or different binder powders and may allow for co-manufacture of otherwise incompatible ingredients or controlled release of the agents.

In certain embodiments, the final compact formed from the coated binder powders disclosed herein may benefit from one or more of the following:
Strength to withstand the rigors experienced during further production, packaging transport and dispensing;
Consistency in form and elimination or reduction in of faults, cracks, chips, contamination, capping etc.
Excellent chemical and physical stability, during normal or harsh storage conditions.

Furthermore, in certain embodiments, the use of the coated binder powders may advantageously allow for more effective or efficient sintering into a resulting solid form, with the sintered solid form having improved properties, such as strength.

EXAMPLES

The following examples serve to illustrate exemplary embodiments of the disclosure and should not be construed as limitations to the generality hereinbefore described.

Example 1

Preparation of Binder Powder

An aqueous solution of PVP 2% (w/w) and L-leucine 0.2% (w/w) was prepared, and then spray dried from a Buchi190 laboratory spray dryer. The liquid was sprayed at approximately 5 ml/min with an outlet temperature of approximately 70° C. Conditions were adjusted to ensure efficient collection in the cyclone of a dry powder.

This process was then repeated with similar parameters except the % w/w of leucine varied between 0.01% and 1%. At higher levels the solubility of the leucine restricted dissolution.

The volume median diameter of the particles was measured at approximately 5 microns. It was found that by adjusting the liquid flow rate and the atomiser air flow, particles with volume median diameter of between about 2 and 10 microns could be made in this system. It should be noted that other spray dryers, such a Niro Mobile Minor, which can achieve larger volume median diameter particles, could be used.

The properties of these materials were then examined.

Example 2

Preparation of Dry Compressed Tablets

Lactose (Pharmatose P450M) was selected as a model powdered active agent to study the formation of tablets.

Additional samples were prepared as follows:
Pharmatose P450M and about 1% (w/w) magnesium stearate were placed in a Hosokawa Micron AMS Mini mechanofusion bowl and the unit was sealed. The unit was configured with a Nobilta 1 mm gap head, with cooling water applied at room temperature. Mechanofusion was conducted at about 500 rpm for about 2 min, and then increased to 4000 rpm for 10 min. This material was recovered while discarding any residue on the lid of the vessel.

The same process was then repeated but the magnesium stearate was replaced with one of:

L-leucine, PRUV (sodium stearyl fumarate), COMPRITROL (glyceryl behenate), fumed silica (hydrophilic Cabosil) or fumed silica (hydrophobic Aerosil R972).

A portion of each of these materials was then gently hand blended by folding with a spatula with 10% w/w of the spray dried material identified in Example 1 comprising 90% PVP and 10% L-leucine of volume equivalent spherical median diameter about 5 microns.

In addition, 10% w/w of the spray dried material identified in Example 1 comprising 90% PVP and 10% L-leucine was also combined with a sample of the commercial tabletting excipient Supertab, some untreated (raw) P450M, and p450M mechanofused (without additives). In addition a number of samples were mixed with 30% w/w of the novel binder.

Each of these powders was then carefully weighed into a tablet compression machine (Carver AutoPellet press, Carver, Inc., Wabash, Ind., USA, supplied by ExTech Equipment Pty Ltd, Victoria Australia) and tablets formed under a fixed set of pressure conditions of applying 7000 lbs onto approximately 500 mg of powder. The tablet hardness in each case was then measured using a Dr. Schleuniger Pharmatron model 6D tablet tester (Pharmatron AG Switzerland). The results are summarised in the Tables 3-1 to 3-3 below.

TABLE 3-1

|  |  | Powder Mass (g) | Tablet Mass (g) | Hardness (N) |
|---|---|---|---|---|
| P 450M Raw | 1 | 0.4998 | — | 127.5 |
|  | 2 | 0.501 | — | 118 |
|  | 3 | 0.4991 | — | 126 |
|  | 4 | 0.4962 | — | 124 |
| Average |  | 0.499025 |  | 123.875 |
| S/D |  | 0.00204 |  | 4.1708 |
| P 450M Raw MF | 1 | 0.4972 | 0.4849 | 125 |
|  | 2 | 0.4971 | 0.4958 | 114 |
|  | 3 | 0.5009 | 0.4988 | 129 |
|  | 4 | 0.4999 | 0.499 | 151 |
| Average |  | 0.498775 | 0.494625 | 129.75 |
| S/D |  | 0.00192 | 0.00664 | 15.5214 |
| P 450M + 1% FS | 1 | 0.4975 | 0.4898 | 138 |
|  | 2 | 0.5004 | 0.4946 | 123 |
|  | 3 | 0.4958 | 0.4854 | 130 |
|  | 4 | 0.5 | 0.496 | 141 |
| Average |  | 0.498425 | 0.49145 | 133 |
| S/D |  | 0.00217 | 0.00482 | 8.12403 |
| P 450M + 1% MgSt | 1 | 0.4968 | 0.4881 | 33 |
|  | 2 | 0.4972 | 0.4918 | 53 |
|  | 3 | 0.4968 | 0.4938 | 45 |
|  | 4 | 0.4977 | 0.496 | 59 |
| Average |  | 0.497125 | 0.492425 | 47.5 |
| S/D |  | 0.00042 | 0.00335 | 11.2398 |
| P 450M Raw + 10% PVP | 1 | 0.4982 | 0.481 | 176 |
|  | 2 | 0.5005 | 0.4942 | 126 |
| P450 – 1.7986 g | 3 | 0.4982 | 0.4944 | 157 |
| PVP – 0.1997 g | 4 | 0.4894 | 0.4787 | 154 |
| Average |  | 0.496575 | 0.487075 | 153.25 |
| S/D |  | 0.00490 | 0.00839 | 20.6135 |
| P 450M Raw MF + 10% PVP | 1 | 0.4986 | 0.4367 | 145 |
|  | 2 | 0.4952 | 0.493 | 149 |
| P450 – 1.8613 g | 3 | 0.5 | 0.4997 | 179 |
| PVP – 0.184 g | 4 | 0.4996 | 0.497 | 171 |
| Average |  | 0.49835 | 0.4816 | 161 |
| S/D |  | 0.00218 | 0.03005 | 16.5730 |

TABLE 3-1-continued

|  |  | Powder Mass (g) | Tablet Mass (g) | Hardness (N) |
|---|---|---|---|---|
| P 450M + 1% FS + 10% PVP | 1 | 0.4969 | 0.4874 | 154 |
|  | 2 | 0.4983 | 0.4934 | 106 |
| P450 – 1.85 g | 3 | 0.493 | 0.4897 | 165 |
| PVP – 0.1849 g | 4 | 0.4993 | 0.499 | 167 |
| Average |  | 0.496875 | 0.492375 | 148 |
| S/D |  | 0.00276 | 0.00506 | 28.5773 |
| P 450M +1% FS + 10% PVP | 1 | 0.4974 | 0.4942 | 67 |
|  | 2 | 0.4973 | 0.4949 | 73 |
| P450 – 1.7982 g | 3 | 0.4988 | 0.495 | 67 |
| PVP – 0.1985 g | 4 | 0.4433 | 0.431 | 60 |
| Average |  | 0.4842 | 0.478775 | 66.75 |
| S/D |  | 0.02727 | 0.03185 | 5.3150 |

TABLE 3-2

|  |  | Powder Mass (g) | Tablet Mass (g) | Hardness (N) |
|---|---|---|---|---|
| P 450M + 1% Comp | 1 | 0.4973 | 0.4915 | 142 |
|  | 2 | 0.4954 | 0.4839 | 111 |
|  | 3 | 0.4984 | 0.498 | 136 |
|  | 4 | 0.4922 | 0.4854 | 136 |
| Average |  | 0.495825 | 0.4897 | 131.25 |
| S/D |  | 0.002715 | 0.006435 | 13.79311 |
| P 450M + 1% PRUV | 1 | 0.4977 | 0.4923 | 55 |
|  | 2 | 0.4993 | 0.4924 | 67 |
|  | 3 | 0.4987 | 0.4851 | 61 |
|  | 4 | 0.4983 | 0.4864 | 66 |
| Average |  | 0.4985 | 0.48905 | 62.25 |
| S/D |  | 0.0006733 | 0.00384751 | 5.5 |
| P 450M + 1% L-L | 1 | 0.5002 | 0.4061 | 59 |
|  | 2 | 0.496 | 0.48 | 58 |
|  | 3 | 0.4997 | 0.4817 | 72 |
|  | 4 | 0.4998 | 0.4817 | 72 |
| Average |  | 0.498925 | 0.482375 | 65.25 |
| S/D |  | 0.001961 | 0.0026094 | 7.804912 |
| P 450M + 1% FS•C | 1 | 0.4983 | 0.4952 | 122 |
|  | 2 | 0.4955 | 0.494 | 133 |
|  | 3 | 0.4982 | 0.4968 | 135 |
|  | 4 | 0.4995 | 0.4984 | 144 |
| Average |  | 0.497075 | 0.4961 | 133.5 |
| S/D |  | 0.001689 | 0.0019148 | 9.036961 |
| P 450M + 1% Comp + 10% PVP | 1 | 0.4998 | 0.4922 | 140 |
|  | 2 | 0.5002 | 0.4953 | 177 |
|  | 3 | 0.4937 | 0.4915 | 169 |
| P450M – 2.0258 PVP – 0.2094 g | 4 | 0.4978 | 0.4923 | 181 |
| Average |  | 0.497875 | 0.492825 | 166.75 |
| S/D |  | 0.002974 | 0.001687 | 18.51800 |
| P 450M + 1% PRUV + 10% PVP | 1 | 0.4971 | 0.4929 | 67 |
|  | 2 | 0.4977 | 0.4917 | 79 |
|  | 3 | 0.5006 | 0.4934 | 92 |
| P450M – 2.0100 g PVP – 02005 g | 4 | 0.4986 | 0.4958 | 83 |
| Average |  | 0.4985 | 0.49345 | 80.25 |
| S/D |  | 0.0015297 | 0.0017214 | 10.372238 |
| P 450M + 1% L-L + 10% PVP | 1 | 0.4907 | 0.4906 | 91 |
|  | 2 | 0.5 | 0.4967 | 72 |
|  | 3 | 0.4993 | 0.4934 | 92 |
| P450M – 1.9743 g PVP – 0.1924 g | 4 | 0.4996 | 0.4929 | 98 |
| Average |  | 0.4994 | 0.49415 | 88.25 |
| S/D |  | 0.000547 | 0.001725 | 11.26572 |
| P 450M + 1% FS•C + 10% PVP | 1 | 0.4954 | 0.4917 | 116 |
|  | 2 | 0.4965 | 0.4902 | 186 |
|  | 3 | 0.4986 | 0.4946 | 186 |
| P450M – 1.9838 g PVP – 0.1946 g | 4 | 0.4993 | 0.498 | 182 |
| Average |  | 0.49745 | 0.490625 | 167.5 |
| S/D |  | 0.001811 | 0.003441 | 34.38507 |

TABLE 3-3

| | | Powder Mass (g) | Tablet Mass (g) | Hardness (N) |
|---|---|---|---|---|
| Lactose | 1 | 0.4992 | 0.4979 | 88 |
| SuperTab | 2 | 0.495 | 0.4945 | 101 |
| | 3 | 0.4987 | 0.4988 | 97 |
| | 4 | 0.497 | 0.4963 | 89 |
| Average | | 0.4974 | 0.4968 | 93.73 |
| S/D | | 0.0018 | 0.0018 | 6.2915 |
| P450M | 1 | 0.4996 | 0.495 | 126 |
| Blended | 2 | 0.4994 | 0.4921 | 130 |
| + 1% FS | 3 | 0.493 | 0.4886 | 111 |
| | 4 | 0.4976 | 0.4922 | 127 |
| Average | | 0.4974 | 0.49197 | 123.5 |
| S/D | | 0.0030 | 0.00262 | 8.504900 |
| Lactose | 1 | 0.4977 | 0.4974 | 129 |
| SuperTab + 10% | 2 | 0.4939 | 0.4915 | 124 |
| PVP | 3 | 0.499 | 0.4917 | 114 |
| S/T – 2.003 g | 4 | 0.4976 | 0.4925 | 122 |
| PVP – 0.1999 g | | | | |
| Average | | 0.4970 | 0.4932 | 122.25 |
| S/D | | 0.0021 | 0.0027 | 6.2383 |
| P450M Blended | 1 | 0.4948 | 0.4944 | 156 |
| + 1% FS + 10% | 2 | 0.5 | 0.4844 | 156 |
| PVP | 3 | 0.4986 | 0.4981 | 155 |
| P450M – 2.0073 g | 4 | 0.4995 | 0.4974 | 166 |
| PVP – 0.1978 g | | | | |
| Average | | 0.4982 | 0.4935 | 158.25 |
| S/D | | 0.0023 | 0.0063 | 5.18812 |
| SuperTab + | 1 | 0.5 | 0.4991 | 121 |
| 30 % PVP | 2 | 0.498 | 0.4941 | 102 |
| | 3 | 0.4999 | 0.4994 | 129 |
| | 4 | 0.4992 | 0.4979 | 143 |
| Average | | 0.4992 | 0.4976 | 123.75 |
| S/D | | 0.0009 | 0.0024 | 17.11480 |
| P450M | 1 | 0.5014 | 0.4977 | 165 |
| Blended + | 2 | 0.4935 | 0.4883 | 151 |
| 1% FS + | 3 | 0.5002 | 0.4997 | 186 |
| 30% PVP | 4 | 0.5001 | 0.4972 | 192 |
| Average | | 0.4988 | 0.4957 | 173.5 |
| S/D | | 0.00358 | 0.0050 | 18.9472 |

Example 3

Example powders were prepared by spray drying. The precursor solutions contained PVP, and water in fixed proportions with only the amount of L-leucine being varied as specified by the formulation. The amount of L-leucine was specified as a percentage of PVP by weight. For example, a 50% L-leucine precursor formulation contains 5000 mg PVP, 250 ml Milli Q water and 2500 mg of L-leucine. In total, 8 precursor formulations were prepared as follows:

0% L-leucine (Control), 2.5% L-leucine, 5% L-leucine, 10% L-leucine, 20% L-leucine, 30% L-leucine, 40% L-leucine and 50% L-leucine.

For all formulations, a BÜCHI 190 Mini spray dryer (BÜCHI Laboratory-Techniques, Flawil, Switzerland) was used with the following spray drying parameters: compressed nitrogen gas was used as the atomising gas, with gas flow rate set at 800 L/minute, solution feed rate: 5 ml/minute and the heating control was set at setting 6. The concerted effect of these settings translated to a consistently observed outlet temperature range of 74-76° C. Powders were collected and stored in a desiccator over silica gel. Particles with VSED in the range 1 to 10 microns were formed.

The 1 ml shear cell test was performed on a Freeman powder rheometer (Freeman Rheology, Worcestershire, UK). Each precursor powder was loaded onto the shear cell until the powder level was parallel to the surface of the shear cell. The shear cell test included a pre conditioning stage, a compression stage and a shear stage. For each powder, the test was performed in triplicate to derive an average cohesion value (kPa) of the powder sample.

Figure 3:
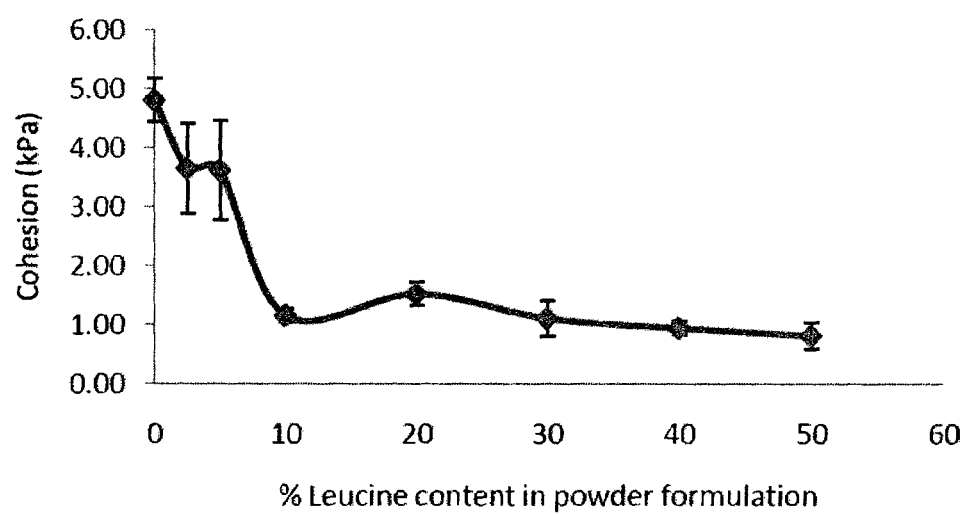
FIG. 3 graphically depicts the effect of % L-leucine content on the cohesion of PVP binder particles.

The shear cell measurements give a cohesion value which provides an indication on how cohesive the powders are in relation to one another. The results are presented in FIG. 3.

It is observed that below a 10% w/w L-leucine content, the cohesion value increases. The spray dried PVP (0% L-leucine content) appears to be the most cohesive. Adding L-leucine reduces the cohesion value. At 10% L-leucine and above, a consistent cohesion is achieved. This suggests that at these L-leucine concentrations, a consistent surface may be produced, implying a complete coverage by the amino acid additive.

Example 4

Lactose (Pharmatose P350M: DMV International) which has a mass median particle size of about 30 μm, was selected as a model fine pharmaceutical powder to study the direct formation of tablets.

Pharmatose P350M powder combined with 1% (w/w) pharmaceutical grade magnesium stearate powder were placed in a Hosokawa Micron AMS Mini mechanofusion bowl and the unit was sealed. The unit was configured with a Nobilta 1 mm gap head, with cooling water applied at room temperature. Mechanofusion was conducted at about 500 rpm for about 2 min, and then increased to 4000 rpm for 10 min. This material was recovered while discarding any residue on the lid of the vessel.

Separately, two further example powders either comprising only spray dried PVP K30, or comprising a co-spray dried powder of PVPK30:L-leucine in a ratio of 93:7 (7.5 wt/wt % leucine) were prepared via a Buchi 190 Mini spray dryer using the same conditions as described in Example 3. Particles having volume median spherical equivalent diameter of less than 10 μm, as measured by Malvern Mastersizer 2000, were produced. A series of powders were then prepared with composition as outlined in the table below. Each of these powder materials was gently hand blended by folding with a spatula for approximately 10 minutes. The mixtures were then brushed through a sieve with aperture size of 500 μm.

For each of these powders, approximately 500 mg was then carefully weighed into the die of a tablet compression machine (Carver AutoPellet press, Carver Inc., Wabash, Ind., USA) and tablets were then formed under a fixed set of pressure conditions (7000 LB or 10000 LB). The tablet hardness in each case was then measured using a Dr. Schleuniger Pharmatron model 6D tablet tester (Pharmatron AG, Switzerland). The results are summarised in Tables 4-1 and 4-2 below.

TABLE 4-1

| Press force 7000 LB 500 mg/tablet | |
|---|---|
| Formulation | Hardness (N) |
| 1. Mechanofused Pharmatose 350M (1% MgSt) | 34 |
| 2. Mechanofused Pharmatose 350M (1% MgSt) mixed with 10% w/w co-spray dried PVP K30 (7% L-leucine) | 61 |

TABLE 4-2

Press force 10000 LB 500 mg/tablet

| Formulation | Hardness (N) | | | | | MEAN (N) | SD (N) |
|---|---|---|---|---|---|---|---|
| 1. Mechanofused Pharmatose 350M (1% MgSt) | 53 | 56 | 52 | 52 | 54 | 53.4 | 1.67 |
| 2. Mechanofused Pharmatose 350M (1% MgSt) mixed with 10% w/w spray dried PVP K30 | 116 | 122 | 100 | 106 | 127 | 114.2 | 11.14 |
| 3. Mechanofused Pharmatose 350M (1% MgSt) mixed with 20% w/w spray dried PVP K30 | Unable to eject tablet due to adhesion to the die | | | | | | |
| 4. Mechanofused Pharmatose 350M (1% MgSt) mixed with 10% w/w co-spray dried PVP K30 (7.5% L-leucine) | 108 | 102 | 108 | 84 | 97 | 99.8 | 9.96 |
| 5. Pharmatose 350M (non-mechanofused) | 142 | 142 | 137 | 159 | 150 | 146 | 8.64 |
| 6. Pharmatose 350M (non-mechanofused) mixed with 10% w/w spray dried PVP K30 | Unable to eject tablet due to adhesion to the die | | | | | | |
| 7. Pharmatose 350M (non-mechanofused) mixed with 20% w/w spray dried PVP K30 | Unable to eject tablet due to adhesion to the die | | | | | | |
| 8. Pharmatose 350M (non-mechanofused) mixed with 10% w/w co-spray dried PVP K30 (7.5% L-leucine) | 251 | 215 | 234 | 160 | 272 | 226.4 | 42.67 |

These examples demonstrate that, addition of the co-spray dried PVP/L-leucine to a host material in all cases significantly increases the hardness of the tablets formed compared to the powders comprising the host material without the addition. This is the case for host powders that have been surface treated by mechanofusion or in their original untreated state. The increases in hardness are approximately 100% in each case, irrespective of the compression press force. It is noted that although Formulations 2 and 4 of Table 4-2 were statistically of comparable hardness, Example 3 demonstrates that PVP binder powders with a leucine content of 0% demonstrate increased cohesiveness. It is also noted that, generally, if a spray dried PVP, without L-leucine, is used in this type of mixture, the powder becomes undesirably stuck into the tablet die making ejection to difficult to perform. Hence, the binder powders of these examples significantly and advantageously increase tablet hardness for a given host powder and compression press force, but also surprisingly enhance tablet ejection form the die, without need for a separate lubricant. These examples show how the binder powder can act as both binder and lubricant in the same composition.

Example 5

In a further example, binder particles containing an exemplary active agent or drug were also prepared. An aqueous suspension comprising of PVP 5.2% (w/v) and l-leucine 0.8% (w/v), polysorbate 80 (acting as a surfactant to allow effective milling) 0.01% (w/v) and indomethacin powder 2% (w/v) was prepared, and this was milled at 2000 rpm (bead size 500 µm) for 3 hours using a DYNO®-mill (Willy A. Bachofen AG—Maschinenfabrik, Switzerland). The particle size distribution of the suspension at each time point was measured using a Malvern Mastersizer® 2000 (Malvern Instruments Ltd., UK), and is presented below in the form of D50 and D90 in Table 5-1:

TABLE 5-1

| Collection time point (minute) | $D_{50}$ (µm) | $D_{90}$ (µm) |
|---|---|---|
| 0 | 4.02 | 8.03 |
| 15 | 1.30 | 3.13 |
| 30 | 0.49 | 1.71 |
| 60 (1 h) | 0.23 | 1.01 |
| 90 (1.5 h) | 0.17 | 0.60 |
| 120 (2 h) | 0.15 | 0.41 |
| 150 (2.5 h) | 0.15 | 0.37 |
| 180 (3 h) | 0.14 | 0.32 |

The milled suspension was then spray dried from a Buchi190 laboratory spray dryer to produce a fine powder. The liquid was sprayed at approximately 5 ml/min with an outlet temperature of approximately 70° C. Conditions were adjusted to ensure efficient collection in the cyclone of a dry powder. As in Examples 3 and 4, dried particles having volume median spherical equivalent diameter of less than 10 µm, as measured by Malvern Mastersizer 2000, were produced. These dry particles also had similar physical powder properties such as cohesion as measured by the Freeman powder rheometer, as the equivalent l-leucine containing powders described in Example 3.

These powders were suitable for use in compression tests with host powders as identified in Examples 2 and 4. However, it was also discovered that this powder could be compressed, without a host powder, directly into tablets as described below.

This spray dried powder (400 mg) was carefully weighed into a tablet compression machine (Carver AutoPellet press, Carver Inc., Wabash, Ind., USA) and tablets formed under a fixed set of pressure conditions (7000 LB). The tablet hardness in each case was then measured using a Dr. Schleuniger Pharmatron model 6D tablet tester (Pharmatron AG, Switzerland). The results are summarised in Table 5-2 below.

TABLE 5-2

Press force 7000 LB 400 mg/tablet

| Formulation | Tablet hardness (N) |
|---|---|
| 1. Original unmodified Indomethacin powder | 99 |
| 2. Spray dried Indomethacin powder comprising PVP, 1-leucine and polysorbate 80 | 122 |

The invention claimed is:

1. A binder powder comprising:
spray-dried coated binder particles comprising core binder particles that are water soluble or wettable and a surface coating of L-leucine, isoleucine or trileucine covering a surface of each core binder particle, the L-leucine, isoleucine or trileucine provided in an effective amount of up to 20% by weight of the core binder particles to form a non-cohesive layer having an average layer thickness of about 1 μm or less on each of the core binder particles; and
wherein at least 80% by mass of the spray-dried coated binder particles have a volume equivalent spherical diameter of about 20 μm or less.

2. The binder powder according to claim 1, wherein the core binder particles are selected from the group consisting of sugars, gelatine, dibasic calcium phosphate, corn (maize); starch, pregelatinized starch, acacia, xanthan gum, tragacanth, gelatine, alginic acid, polyethylene glycol, polyvinyl alcohols, polyvinylcaprolactam, polymethacrylates, polyvinylpyrrolidone (PVP), polyvinylpyrrolidone-vinyl acetate (PVP-V A), polyvinylcaprolactam-polyvinyl acetate-polyethylene glycol, methacrylic acid-ethylacrylate, polyvinylpyrrolidone and polyvinyl acetate, hydroxypropyl methylcellulose (HPMC), methyl cellulose, ethyl cellulose, hydroxyl propyl cellulose (HPC), hydroxyethylcellulose (HEC), and sodium carboxy methyl cellulose.

3. The binder powder according to claim 1, wherein the core binder particles are a polymer, a co-polymer, or a mixture of polymers.

4. The binder powder according to claim 3, wherein the core binder particles are polyvinylpyrrolidone (PVP).

5. The binder powder according to claim 1, wherein the effective amount of the L-leucine, isoleucine or trileucine is about 2.5% to 15% by weight of the core binder particles.

6. The binder powder according to claim 1 wherein the volume equivalent spherical diameter of the coated binder particles is about 10 μm or less.

7. The binder powder according to claim 1, wherein the volume equivalent spherical diameter of the coated binder particles is about 5 μm or less.

8. The binder powder according to claim 1, wherein the non-cohesive layer of L-leucine, isoleucine or trileucine covers at least 40 percent of a total area of the surface of each core binder particle.

9. A binder powder comprising:
spray-dried binder particles including core binder particles that are water soluble or wettable and a non-cohesive surface coating agent of L-leucine, isoleucine or trileucine coated on a surface of each individual core binder particle, wherein the core binder particles are a polymer, a co-polymer, or a mixture of polymers; the L-leucine, isoleucine or trileucine provided in an effective amount of about 2.5% to 15% by weight of the core binder particles to provide a non-cohesive surface layer having an average layer thickness of about 1 μm or less on each of the core binder particles; and
wherein at least 80% by mass of the spray-dried binder particles have a volume equivalent spherical diameter of about 20 μm or less.

10. The binder powder according to claim 9, wherein the volume equivalent spherical diameter of the at least 80% by mass of the spray-dried binder particles is about 10 μm or less.

11. The binder powder according to claim 9, wherein the core binder particles comprise polyvinylpyrrolidone (PVP).

12. The binder powder according to claim 9, wherein at least one of the effective amount of the L-leucine, isoleucine or trileucine is about 7.5% to 10% by weight of the core binder particles, and the non-cohesive surface layer of L-leucine, isoleucine or trileucine covers on average at least 50% of the surface of each of the core binder particles.

13. The binder power according to claim 1, wherein the spray-dried coated binder particles further comprise one or more active or functional ingredients.

14. The binder power according to claim 13, wherein the one or more active or functional ingredients comprise an antimicrobial, analgesic, anti-depressant, anti-psychotic, anti-inflammatory, anti-arrhythmic, anti-coagulant, anti-cholesterol, anticonvulsant, anti-spasmodic, anti-arthritic, anti-ulcer agent, anti-hypertensive, anti-diabetic, diuretic, sedative or tranquilizer, amino acid, mineral, or vitamin.

15. A dry powder blend comprising a binder powder according to claim 1 together with at least one of a carrier and an active or functional ingredient.

16. A method of preparing coated binder particles, comprising:
spray-drying a liquid mixture of a binder that is water soluble or wettable and L-leucine, isoleucine or trileucine in an effective amount of up to 20% by weight of the binder to form fine spray-dried coated binder particles each with a binder core and a non-cohesive coating layer of L-leucine, isoleucine or trileucine having an average layer thickness about 1 μm or less on a surface of the binder core of the fine spray-dried coated binder particles;
wherein at least 80% by mass of the fine spray-dried coated binder particles have a volume equivalent spherical diameter of about 20 μm or less.

17. The method according to claim 16, wherein the liquid mixture further includes one or more active or functional ingredients such that on spray-drying the fine spray-dried coated binder particles are formed with the binder core and the non-cohesive coating layer of L-leucine, isoleucine or trileucine together with the one or more active or functional ingredients.

18. The method according to claim 16, wherein the binder is a polymer, a co-polymer, or a mixture of polymers.

19. The method according to claim 18, wherein the binder is polyvinylpyrrolidone (PVP).

20. The method according to claim 16, wherein the effective amount of the L-leucine, isoleucine or trileucine is about 2.5% to 15% by weight of the binder.

* * * * *